(12) United States Patent
Steinmetz

(10) Patent No.: US 10,194,859 B2
(45) Date of Patent: *Feb. 5, 2019

(54) ACTIVITY REGULATION BASED ON BIOMETRIC DATA

(71) Applicant: Barcoding, Inc., Baltimore, MD (US)

(72) Inventor: Jay Steinmetz, Baltimore, MD (US)

(73) Assignee: Barcoding Inc., Baltimore, MD (US)

( * ) Notice: Subject to any disclaimer, the term of this patent is extended or adjusted under 35 U.S.C. 154(b) by 606 days.

This patent is subject to a terminal disclaimer.

(21) Appl. No.: 14/850,791

(22) Filed: Sep. 10, 2015

(65) Prior Publication Data

US 2016/0000371 A1    Jan. 7, 2016

Related U.S. Application Data

(63) Continuation of application No. 13/560,189, filed on Jul. 27, 2012, now Pat. No. 9,155,460.

(51) Int. Cl.
| | |
|---|---|
| *A61B 5/00* | (2006.01) |
| *A61B 3/00* | (2006.01) |
| *A61B 5/0205* | (2006.01) |
| *G09B 5/00* | (2006.01) |
| *A61B 5/11* | (2006.01) |
| *A61B 5/18* | (2006.01) |

(Continued)

(52) U.S. Cl.
CPC ............... *A61B 5/486* (2013.01); *A61B 3/00* (2013.01); *A61B 3/10* (2013.01); *A61B 5/002* (2013.01); *A61B 5/0022* (2013.01); *A61B 5/0205* (2013.01); *A61B 5/02055* (2013.01); *A61B 5/1112* (2013.01); *A61B 5/1113* (2013.01); *A61B 5/1118* (2013.01); *A61B 5/14542* (2013.01); *A61B 5/18* (2013.01); *A61B 5/6803* (2013.01); *A61B 5/7246* (2013.01); *A61B 5/741* (2013.01); *A61B 7/00* (2013.01); *G06F 19/00* (2013.01); *G09B 5/00* (2013.01); *G16H 40/67* (2018.01); *A61B 5/01* (2013.01); *A61B 5/021* (2013.01); *A61B 5/024* (2013.01); *A61B 5/02438* (2013.01); *A61B 5/08* (2013.01); *A61B 5/082* (2013.01); *A61B 5/145* (2013.01); *A61B 2505/07* (2013.01)

(58) Field of Classification Search
CPC ............ A63B 24/0062; A63B 24/0075; G06F 19/3481
USPC ..................... 434/247; 482/4, 8, 92
See application file for complete search history.

(56) References Cited

U.S. PATENT DOCUMENTS

| | | | | |
|---|---|---|---|---|
| 5,581,484 A | * | 12/1996 | Prince ..................... | G06F 3/014 340/407.1 |
| 7,662,065 B1 | * | 2/2010 | Kahn ................. | A63B 24/0062 434/247 |

(Continued)

*Primary Examiner* — Thomas Hong
*Assistant Examiner* — Sadaruz Zaman
(74) *Attorney, Agent, or Firm* — Occhiuti & Rohlicek LLP

(57) ABSTRACT

Disclosed are devices, systems, apparatus, methods, products, and other implementations, including a method that includes obtaining biometric data of a user, and generating instruction data, presentable on a user interface, based on data relating to one or more activities to be completed by the user and based on the biometric data of the user. In some embodiments, obtaining the biometric data may include measuring one or more of, for example, heart rate, blood pressure, blood oxygen level, temperature, speech-related attributes, breath, and/or eye behavior.

17 Claims, 6 Drawing Sheets

(51) Int. Cl.
*A61B 3/10* (2006.01)
*A61B 7/00* (2006.01)
*G06F 19/00* (2018.01)
*G16H 40/67* (2018.01)
*A61B 5/021* (2006.01)
*A61B 5/024* (2006.01)
*A61B 5/08* (2006.01)
*A61B 5/145* (2006.01)
*A61B 5/01* (2006.01)

(56) References Cited

U.S. PATENT DOCUMENTS

| | | | |
|---|---|---|---|
| 7,905,815 B2* | 3/2011 | Ellis | A61B 5/1038 340/500 |
| 8,204,786 B2* | 6/2012 | LeBoeuf | G16H 50/30 705/14.66 |
| 8,506,396 B1* | 8/2013 | Snyder | G06F 19/3481 463/31 |
| 2007/0078919 A1* | 4/2007 | Westerman | G06F 3/0235 708/200 |
| 2008/0146892 A1* | 6/2008 | LeBoeuf | A61B 5/486 600/300 |
| 2008/0176713 A1* | 7/2008 | Olivera Brizzio | A63B 24/00 482/8 |
| 2009/0009284 A1* | 1/2009 | Sako | A61B 5/7445 340/5.82 |
| 2009/0039886 A1* | 2/2009 | White | G01R 33/28 324/318 |
| 2009/0098519 A1* | 4/2009 | Byerly | G09B 23/28 434/247 |
| 2009/0141938 A1* | 6/2009 | Lim | G06K 9/00664 382/103 |
| 2009/0237511 A1* | 9/2009 | DeFlumere | H04N 5/33 348/164 |
| 2010/0021010 A1* | 1/2010 | Zhang | G06K 9/4647 382/104 |
| 2010/0113153 A1* | 5/2010 | Yen | A63F 13/06 463/37 |
| 2010/0259471 A1* | 10/2010 | Takano | G02B 27/017 345/156 |
| 2011/0243553 A1* | 10/2011 | Russell | G06Q 30/0631 398/25 |
| 2011/0261079 A1* | 10/2011 | Ingrassia, Jr. | A63B 24/0062 345/665 |
| 2012/0077641 A1* | 3/2012 | Dyer | A63B 22/00 482/8 |
| 2012/0252580 A1* | 10/2012 | Dugan | A63F 13/31 463/42 |
| 2013/0012790 A1* | 1/2013 | Horseman | G06F 19/3418 600/301 |
| 2013/0115584 A1* | 5/2013 | Gordon | G09B 19/0038 434/247 |
| 2013/0133055 A1* | 5/2013 | Ali | H04L 63/0861 726/7 |
| 2014/0030684 A1* | 1/2014 | Steinmetz | G09B 5/00 434/247 |

* cited by examiner

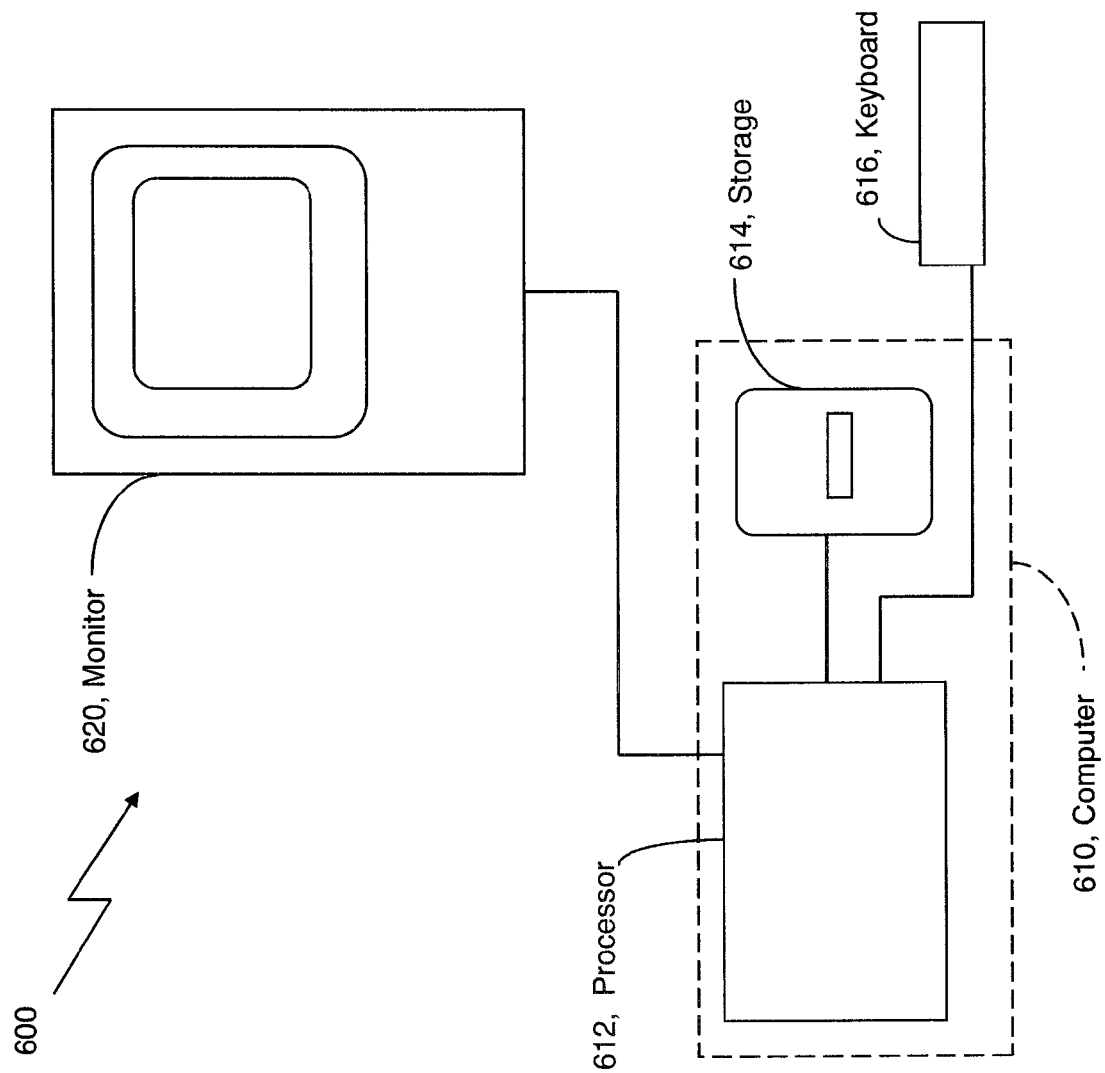

ACTIVITY REGULATION BASED ON BIOMETRIC DATA

CROSS-REFERENCE TO RELATED APPLICATIONS

This application is a continuation application of, and claims priority to, U.S. patent application Ser. No. 13/560,189, entitled "ACTIVITY REGULATION BASED ON BIOMETRIC DATA," and filed Jul. 27, 2012, the content of which is incorporated herein by reference in its entirety.

BACKGROUND

Individuals engaged in various physical activities (be it recreational activities or a work-related activities) are at risk of suffering an injury due to their inability to properly monitor their level of physical exertion, or heed signs of worsening physical condition. When an individual does become aware of his/her increased level of physical exertion resulting from an activity he/she is performing, it is often at a point where the only recourse for avoiding injury is for the individual to immediately cease the physical activity in question.

SUMMARY

The devices, methods, products, systems, apparatus, and other implementations described herein include a method including obtaining biometric data of a user, and generating instruction data, presentable on a user interface, based on data relating to one or more activities to be completed by the user and based on the biometric data of the user.

Embodiments of the method may include at least some of the features described in the present disclosure, including one or more of the following features.

Generating the instruction data based on the data relating to the one or more activities to be completed by the user and based on the biometric data of the user may include revising an initial schedule for collecting and distributing a plurality of items at multiple geographical locations based on the biometric data of the user.

Revising the initial schedule may include adjusting item collection and distribution goals set for the user based on the biometric data of the user. Adjusting the item collection and distribution goals set for the user may include reducing the item collection and distribution goals set for the user in response to a determination, based on the biometric data of the user, that the user's physical exertion level is high. Reducing the item collection and distribution goals may include reducing the item collection and distribution goals in response to a determination that measured heart rate of the user exceeds a predetermined heart rate threshold.

Generating the instruction data may include generating location instructions presentable to the user to direct the user to the multiple geographical locations where item collection and distribution operations for the plurality of items are performed.

The method may further include measuring motion and orientation of the user. Generating the location instructions to direct the user to the multiple geographical locations may include generating the location instructions based, at least in part, on the measured motion and/or orientation of the user.

The method may further include determining location of the user based on signals received from at least one of, for example, a wireless access point, a cellular base station, and/or one or more satellites of a satellite positioning system. Generating the location information to direct the user to the multiple geographical locations may include generating the location instructions based, at least in part, on the determined location of the user.

The method may further include presenting the instruction data on an audio interface attachable to at least one of the user's ears. The audio interface attachable to the at least one of the user's ears may include one or more biometric sensors coupled to a housing of the audio interface, the one or more biometric sensors configured to measure at least some of the user's biometric attributes.

The method may further include transmitting to a server located remotely from the user the biometric data, and receiving from the remotely located server the instruction data, the instruction data generated remotely at the server.

Generating the instruction data may include generating the instruction data at a controller coupled to biometric sensors configured to measure the user's biometric attributes.

Obtaining the biometric data may include measuring one or more of, for example, heart rate, blood pressure, blood oxygen level, temperature, speech-related attributes, breath, and/or eye behavior.

The method may further include disabling at least part of user equipment of the user in response to a determination that at least one of measured biometric attributes represented by the obtained biometric data exceeds a corresponding predetermined health indicator threshold. Disabling the at least part of the user equipment may include disabling the at least part of the user equipment in response to a determination that measured heart rate of the user exceeds a predetermined heart rate threshold.

In some variations, a system is provided. The system includes one or more biometric sensors to measure one or more biometric attributes of a user, and a controller to generate instruction data, presentable on a user interface, based on data relating to one or more activities to be completed by the user and based on biometric data representative of the one or more biometric attributes of the user measured by the one or more sensors.

Embodiments of the system may include at least some of the features described in the present disclosure, including at least some of the features described above in relation to the method, as well as one or more of the following features.

The controller configured to generate the instruction data based on the data relating to the one or more activities to be completed by the user and based on the biometric data of the user may be configured to revise an initial schedule for collecting and distributing a plurality of items at multiple geographical locations based on the biometric data of the user.

The controller configured to revise the initial schedule may be configured to adjust item collection and distribution goals set for the user based on the biometric data of the user, including to reduce the item collection and distribution goals set for the user in response to a determination, based on the biometric data of the user, that the user's physical exertion level is high.

The system may further include one or more motion sensors to measure motion and/or orientation of the user. The controller configured to generate the instruction data may be configured to generate location instructions presentable to user, based at least in part on the measured motion and orientation of the user, to direct the user to the multiple geographical locations where item collection and distribution operations for the plurality of items are performed.

The system may further include location determination unit to determine location of the user based on signals received from at least one of, for example, a wireless access point, a cellular base station, and/or one or more satellites of a satellite positioning system. The controller configured to generate the instruction data may be configured to generate location instructions presentable to user based, at least in part, on the determined location of the user, to direct the user to the multiple geographical locations where item collection and distribution operations for the plurality of items are performed.

The system may further include an audio interface attachable to at least one of the user's ears to present the generated instruction data. The audio interface attachable to the at least one of the user's ears may include at least one of the one or more biometric sensors, the one or more biometric sensors coupled to a housing of the audio interface.

The system may further include a communication module configured to transmit to a server located remotely from the user the biometric data, and receive from the remotely located server the instruction data, the instruction data generated remotely at the server.

The one or more biometric sensors may include one or more of, for example, a heart rate monitor, a blood pressure monitor, a blood oxygen monitor, a thermometer, a speech sensor, a breath sensor, and/or an eye sensor.

The controller may further be configured to disable at least part of user equipment of the user in response to a determination that biometric data representative of at least one of the one or more biometric attributes exceeds a corresponding predetermined health indicator threshold.

In some variations, a device is disclosed. The device includes an audio interface attachable to at least one ear of a user, one or more biometric sensors coupled to the audio interface, the one or more biometric sensors configured to measure one or more biometric attributes of the user, and a controller to present on the audio interface instruction data generated based on data relating to one or more activities to be completed by the user and based on biometric data representative of the measured one or more biometric attributes of the user.

Embodiments of the system may include at least some of the features described in the present disclosure, including at least some of the features described above in relation to the method and the system.

In some variations, a non-transitory computer readable media is provided. The computer readable media includes computer instructions executable on a processor that, when executed, cause operations including obtaining biometric data of a user, and generating instruction data, presentable on a user interface, based on data relating to one or more activities to be completed by the user and based on the biometric data of the user.

Embodiments of the computer readable media include at least some of the features described in the present disclosure, including at least some of the features described above in relation to the method, the system, and the device.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, is meant to encompass variations of ±20% or ±10%, ±5%, or +0.1% from the specified value, as such variations are appropriate to in the context of the systems, devices, circuits, methods, and other implementations described herein. "Substantially" as used herein when referring to a measurable value such as an amount, a temporal duration, a physical attribute (such as frequency), and the like, is also meant to encompass variations of ±20% or ±10%, ±5%, or +0.1% from the specified value, as such variations are appropriate to in the context of the systems, devices, circuits, methods, and other implementations described herein.

As used herein, including in the claims, "and" as used in a list of items prefaced by "at least one of" or "one or more of" indicates that any combination of the listed items may be used. For example, a list of "at least one of A, B, and C" includes any of the combinations A or B or C or AB or AC or BC and/or ABC (i.e., A and B and C). Furthermore, to the extent more than one occurrence or use of the items A, B, or C is possible, multiple uses of A, B, and/or C may form part of the contemplated combinations. For example, a list of "at least one of A, B, and C" may also include AA, AAB, AAA, BB, etc.

Unless defined otherwise, all technical and scientific terms used herein have the same meaning as commonly understood by one of ordinary skill in the art to which this disclosure belongs.

Details of one or more implementations are set forth in the accompanying drawings and in the description below. Further features, aspects, and advantages will become apparent from the description, the drawings, and the claims.

BRIEF DESCRIPTION OF THE DRAWINGS

These and other aspects will now be described in detail with reference to the following drawings.

FIG. 6 is a schematic diagram of a generic computing system.

Like reference symbols in the various drawings indicate like elements.

DETAILED DESCRIPTION

Disclosed herein are headgears, devices, methods, and various implementations, including a method to regulate user's activities that includes obtaining biometric data of a user (e.g., using one or more biometric sensors measuring one or more biometric attributes), and generating instruction data (also referred to herein as direction data), presentable on a user interface (e.g., audio and/or visual interfaces such as, for example, ear phones, a smartphone carried by the user, a tablet device, such as an iPad™, etc.), based on data relating to one or more activities to be completed by the user and based on the measured biometric data of the user. For example, in some implementations the activities to be regulated are manual labor tasks, such as picking or distributing items in a warehouse. As will be described in greater details below, to ensure the person performing such tasks does not become physically over-exerted, the user's pace/rate for performing those activities (which may be governed according to a predetermined schedule prepared/assigned for that user) may be regulated based on biometric data collected, in real-time (or near-real time), from the user, so that if a determination is made that the user is becoming overly-exerted (as may be indicated by an increased heart rate as measured by a heart monitor), user instructions may be generated and presented to the user via one or more interfaces carried by the user to decrease the user's physical pace.

In some embodiments, the user may be following an initial schedule setting the tasks that need to be completed and/or the goals that are to be completed (e.g., completing a specified number of tasks, such as collecting a specified number of items, within a predetermined period of time). Under such circumstances, generating the instruction data may include revising that schedule for performing the tasks (e.g., reducing or otherwise adjusting the number of tasks that need to be completed in the specified predetermined period of time). Separate presentable instructions/directions may be generated based on the revised schedule. For example, in response to a determination that a user's level of a certain biometric attribute exceeds some predetermined threshold while the user is attempting to complete a certain number of tasks in a particular period of time, the number of tasks that that user needs to complete in the same particular period of time may be reduced. Alternatively and/or additionally, the period of time during which the number of tasks that were assigned to the user may be extended. Additionally and/or alternatively, a schedule for completing the tasks assigned to the user may be adjusted to reflect the adjustment to either the number of tasks to be completed and/or the period of time during which the tasks (the original number of tasks or the revised number of tasks) may be completed.

Figure 1:
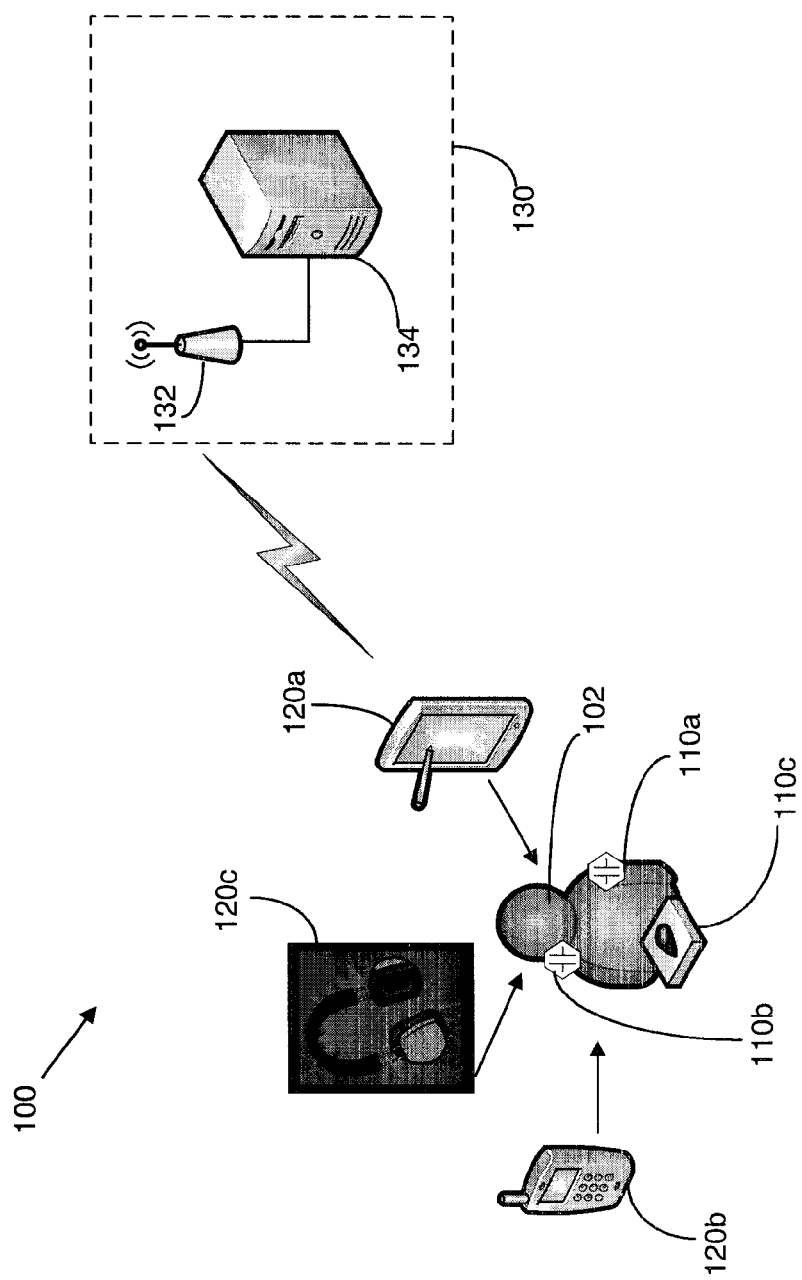
FIG. 1 is a diagram of an example system to regulate users' activities based on biometric data of one or more users.

Thus, with reference to FIG. 1, a diagram of an example system 100 to regulate various user activities (e.g., various physical activities, be it work-related activities or leisure activities) based on biometric data of a user is shown. The system 100 includes one or more biometric sensors 110a-c, each configured to measure biometric attributes of a user 102. The one or more biometric sensors 110a-c may include one or more of, for example, a heart rate monitor, a blood pressure monitor, a blood oxygen monitor, and/or thermometer. Other types of sensors/detectors/monitors to measure biometric attributes of a person may also be used.

As further depicted in FIG. 1, instruction/direction data to regulate the user's activities is presented to a user via one or more interfaces, which may be audio and/or visual interfaces. Example of such interfaces include, for example, a tablet-type device 120a (such as an iPad™), and/or a smartphone device 120b (or any other type of a mobile device) configured to receive and/or transmit cellular and/or wireless communications. In some embodiments, the interface device to present instruction data to regulate the wearer's activities may be earphones 120c. The Earphones 120c generally will include a communication device, e.g., a wireless transceiver, or other types of transceivers to enable communication with a remote device based on any type of communications protocol or technology. Any of the depicted interfaces and the remote system may be elements in various types of communications networks, including a wide area wireless network (WWAN), a wireless local area network (WLAN), a wireless personal area network (WPAN), and so on. A WWAN may be a Code Division Multiple Access (CDMA) network, a Time Division Multiple Access (TDMA) network, a Frequency Division Multiple Access (FDMA) network, an Orthogonal Frequency Division Multiple Access (OFDMA) network, a Single-Carrier Frequency Division Multiple Access (SC-FDMA) network, a WiMax (IEEE 802.16), and so on. A CDMA network may implement one or more radio access technologies (RATs) such as cdma2000, Wideband-CDMA (W-CDMA), and so on. Cdma2000 includes IS-95, IS-2000, and/or IS-856 standards. A TDMA network may implement Global System for Mobile Communications (GSM), Digital Advanced Mobile Phone System (D-AMPS), or some other RAT. GSM and W-CDMA are described in documents from a consortium named "3rd Generation Partnership Project" (3GPP). Cdma2000 is described in documents from a consortium named "3rd Generation Partnership Project 2" (3GPP2). 3GPP and 3GPP2 documents are publicly available. The contents of the above-mentioned documents is hereby incorporate by reference in their entireties. A WLAN may include, for example, an IEEE 802.11x network. A WPAN may include, for example, a Bluetooth network, an IEEE 802.15x, RDID-based networks, other near-field communication networks, etc. In some variations, communication between any of the interfaces 120a-c and a remote system may be implemented based on any combination of the WWAN, WLAN and/or the WPAN described herein.

As will be described in greater details below, in some implementations, at least some of the biometric sensors to measure the person's biometrics may be directly coupled to, or housed in, the housing of the one or more user interfaces through which instruction data is presented to the user. For example, one or more biometric sensors, for example, a heart rate monitor, may be coupled to one of the ear-piece portions of the earphones 120c such that when the user wears the earphones, the heart rate monitor (or some other biometric sensor) is placed proximate to the user's ear, or may even come in contact with the user's ear, to thus enable biometric measurements (heart rate measurements, in this example) to be performed. In some embodiments, one or more of the biometric sensors may be positioned proximate to other locations on the user's body. For example, heart monitor electrodes (e.g., disc-shaped electrodes that include an adhesive layer coating the surface of the disc that contacts the user's body) may be placed at any appropriate place on the body to enable sensing and measuring a person's heart rate.

With continued reference to FIG. 1, as noted, the one or more of the interfaces 120a-c are configured to communicate with a remote system/device, such as a remote system 130. The remote system may include a server 134 and a wireless access point 132, which may include an antenna, a transceiver module and/or a processing unit (not shown) configured to process received signals (e.g., perform filtering and/or demodulation operations in accordance with which ever communication technique technology is implemented for the system 100 of FIG. 1), as well as to process signals to be transmitted via the access point 132 of the remote system 130. The server 134 may maintain data about the activities that need to be performed by the particular user 102 and/or by other users. The list of activities may be used, in part, to generate the instruction/direction data provided to the user 102 and/or to other users. For example, the list of activities (which may be a global list of all activities that need to be completed) may be used, together with biometric data obtained from sensors measuring users' biometric attributes, to prepare and/or revise individual schedules for various users with the tasks that those users need to complete. In some embodiments, the access point 132 may be a public access point (e.g., a public access points serving multiple independent devices), and may in turn communicate wirelessly with the server 134. Additionally and/or alternatively, the access point 132 may be configured to interface with a packet-based network (such as the public Internet) and communicate communication received from the interfaces 120a-c to the packet-based network (after performing appropriate signal processing operations such as operations required to transmit the information received as packets via the packet network). The data transmitted via the packet-based network may be communicated to the server 134, which in turn may be configured to provide the one or more interfaces 120a-c, based on information it received, data relating to activities to be performed by the user carrying the one or more interfaces 120a-c. In some variations, the server 134 and the access point 132 may be a single, integral device.

Figure 2:
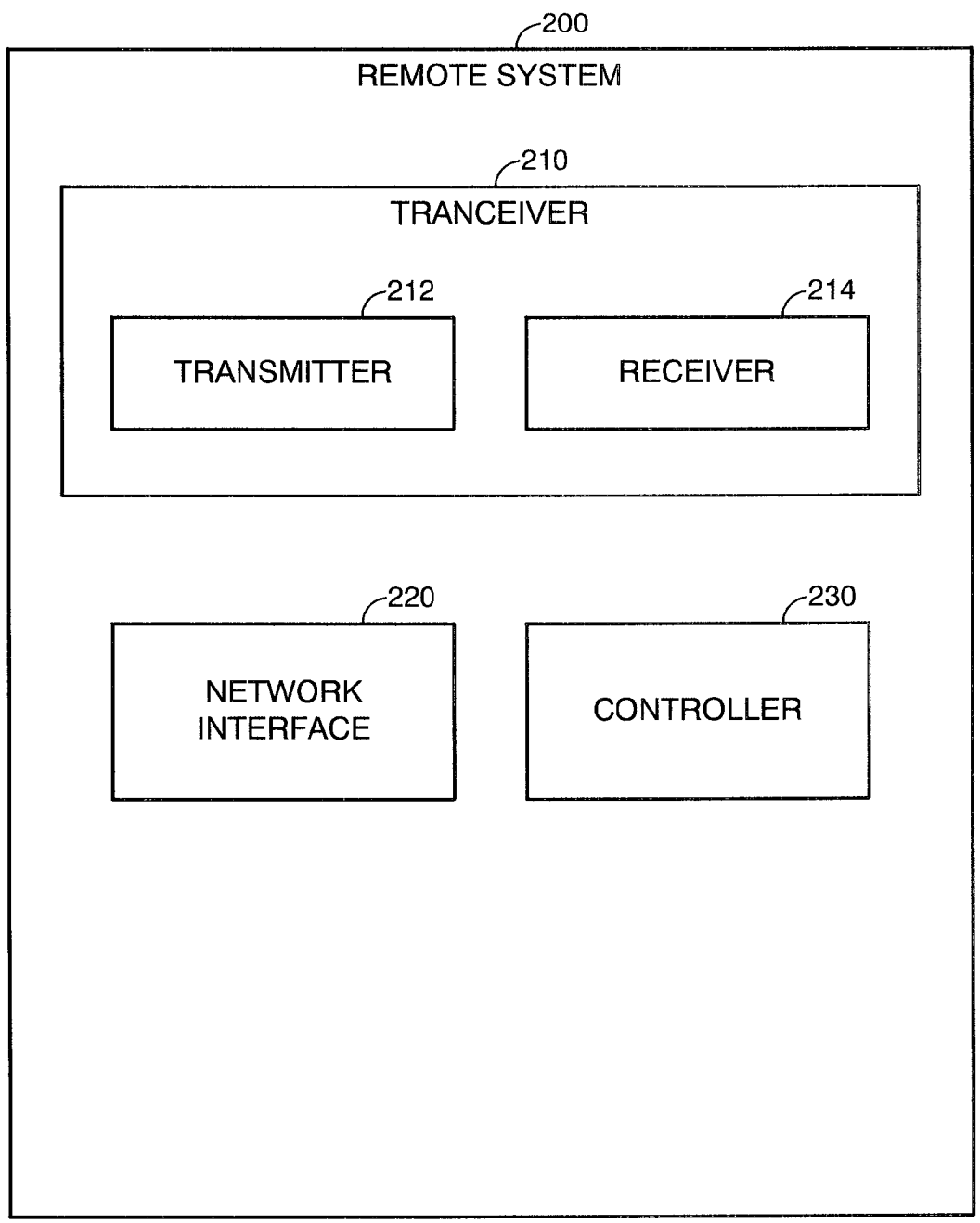
FIG. 2 is a schematic diagram of an example remote system, which may be similar to the remote system depicted in FIG. 1.

With reference now to FIG. 2, a schematic diagram of an example remote system 200, which may be similar to, and be configured to have a functionality similar to that of the remote system 130 depicted in FIG. 1, is shown. The remote system 200 may include a transceiver 210 for communicating with wireless nodes/elements. Such wireless nodes or element may include, for example, an interface (equipped with a communication module) to present instruction data to a user on an interface device (such as any one of the audio and/or visual interface devices 120a-c of FIG. 1), a biometric sensor (equipped with a communication module) configured to establish a communication link with the remote system, etc. The transceiver 210 may include a transmitter 212 for sending signals and a receiver 214 for receiving signals (e.g., uplink messages). The transmitter 210 may be used to implement an access point such as the access point 132 of FIG. 1. In some implementations, the remote system 200 may include a network interface 220 to communicate with other network devices. For example, the remote system may be configured to communicate (e.g., wired or wireless backhaul communication) with a gateway, or other suitable entity of a network, coupled to a packet-based network.

The remote system 200 also includes a controller 230 (also referred to as a processing unit) to manage communications with other network elements (e.g., sending and receiving messages) and to provide other related functionality. The controller 230 may correspond to the implementation of the server 134 depicted in FIG. 1. In some implementations, the controller is configured to receive biometric-based data corresponding to measurements performed by the one or more biometric sensors and to generate, based on that received data, data to enable regulating a user's activities. For example, the controller 230 may determine the user's level of exertion resulting from the activities the user is performing or undertaking, and generate data in response thereto that can be used to regulate the user's activities. Such generated data may include actual instruction data to be presented on the interface(s) carried by the user to instruct the user (e.g., verbally, through visual cues, through tactile cues, etc.) how to perform the activities the user is supposed to perform. For example, the biometric data may be indicative of high heart rate (e.g., as determined from a comparison of a predetermined heart rate threshold value to a heart rate indicated by the received data, or derived from the received data, and/or when the heart rate has deviated by some predetermined value or percentage from a baseline value), and in response to the determination of the high heart rate, the controller 230 may generate instruction data instructing the user to slow down. Alternatively or additionally, the system 200 may maintain (e.g., in a storage device coupled to the processing unit) a schedule of tasks to be performed by the user, or data representative of goals to be accomplished by the user (e.g., completing some specified number of tasks, such as picking up a specified number of objects/items in a warehouse). In response to a determination of excessive user exertion level, the schedule of tasks and/or the specified goals may be adjusted so that a lighter, less demanding, schedule or goals are determined for the user, thus enabling a decrease of the user's exertion level. In some implementations, the remote system 200 may be monitoring, managing/controlling multiple users, and can also adjust the activities to be accomplished by other users in response to an adjustment of a particular user's tasks. For example, if a particular user's tasks to be performed have been reduced because of a determination that that user's exertion level is too high, the tasks that will no longer be performed by that user can be assigned to another user whose level of exertion is normal or even sub-normal. Thus, individual adjustments of the activities to be performed by one user may cause adjustments to the activities to be performed by other users. The controller/processing unit may be implemented, in some embodiments, as a processor-based device, with a configuration similar to that shown and described in relation to FIG. 6.

In some implementations, performing at least some of the operations to regulate the activities performed by the user (e.g., the user 102 shown in FIG. 1) is done at one or more of the devices carried by the user 102, including, for example, one or more of the interfaces 120a-c and/or one or more of biometric sensors 110a-c. Thus, with reference to FIG. 3, a schematic diagram illustrating various components of an example device 300, which may have a structural or functional configuration that is at least partly similar to that of the various devices 110a-c and/or 120a-c, is shown. It is to be noted that one or more of the modules and/or functions illustrated in the example of FIG. 3 may be further subdivided, or two or more of the modules or functions illustrated in FIG. 3 may be combined. Additionally, one or more of the modules or functions illustrated in FIG. 3 may be excluded.

As shown, the example device 300 may include one or more transceivers (e.g., LAN transceiver 306, WLAN transceiver 304, etc.) that may be connected to one or more antennas 302. The transceivers 304 and 306 may comprise suitable devices, hardware, and/or software for communicating with and/or detecting signals to/from a network or remote system (such as the remote system 130 or 200 depicted in FIGS. 1 and 2 respectively) and/or directly with other wireless devices within a network. As noted, by way of example only, in some embodiments, the transceiver 306 may enable wireless LAN communication (e.g., WLAN, such as WiFi-based communications) to thus cause the device 300 to be part of a WLAN implemented as an IEEE 802.11x network. In some embodiments, the transceiver 304 may enable the device 300 to communicate with one or more cellular access points (also referred to as a base station) used in implementations of Wide Area Network Wireless Access Points (WAN-WAP), which may be used for wireless voice and/or data communication. A wireless wide area network (WWAN) may be part of a Code Division Multiple Access (CDMA) network, a Time Division Multiple Access (TDMA) network, a Frequency Division Multiple Access (FDMA) network, an Orthogonal Frequency Division Multiple Access (OFDMA) network, a Single-Carrier Frequency Division Multiple Access (SC-FDMA) network, a WiMax (IEEE 802.16), and so on. As noted, a CDMA network may implement one or more radio access technologies (RATs)

such as cdma2000, Wideband-CDMA (W-CDMA), and so on. Cdma2000 includes IS-95, IS-2000, and/or IS-856 standards, and a TDMA network may implement Global System for Mobile Communications (GSM), Digital Advanced Mobile Phone System (D-AMPS), or some other RAT. In some variations, the transceivers 304 and 306 (and/or some other transceiver used in implementations of the device 300) may enable the device 300 to communicate according to other types of wireless networking technologies, for example, Ultra Wide Band, ZigBee, wireless USB, etc.

Figure 3:
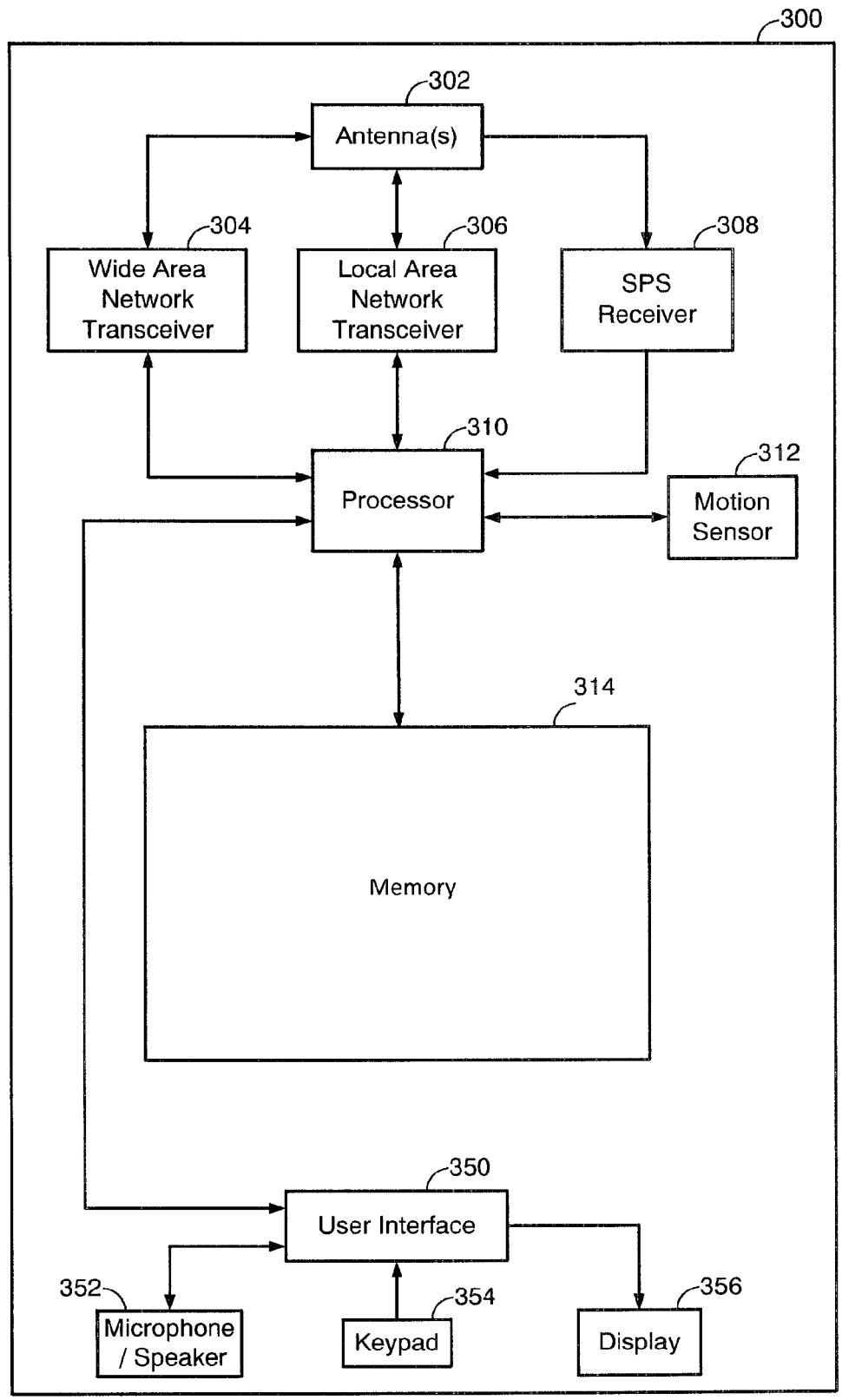
FIG. 3 is a schematic diagram illustrating various components of an example device that may be carried by a user whose activities are to be regulated.

As further illustrated in FIG. 3, in some embodiments, an SPS receiver 308 may also be included in the device 300. The SPS receiver 308 may be connected to the one or more antennas 302 for receiving satellite signals. The SPS receiver 308 may comprise any suitable hardware and/or software for receiving and processing SPS signals. The SPS receiver 308 may request information as appropriate from the other systems, and may perform the computations necessary to determine the device's 300 position using, in part, measurements obtained by any suitable SPS procedure. Such positioning information may be used, for example, to determine the location and motion of the user, and to instruct/direct the user in accordance with that positioning information. For example, a user tasked with performing physical activities within some geographical area may be aided to reach various locations at that geographical area based on data received by the SPS receiver. Additionally and/or alternatively, the device 300 may derive positioning information based on signals communicated to and from access points (and/or base stations), e.g., by performing multilateration position determination procedures based on metrics derived from the communicated signals. Such metrics from which the device 300's position may be determined include, for example, round trip time (RTT, which generally corresponds to the length of time it takes a signal to be sent from a mobile device to an access point, and to receive from the access point a reply thereto), received signal strength indication (RSSI, which is an indication of a signal power level of a signal received by an antenna of the mobile device), etc.

In some embodiments, a motion/orientation sensor 312 may be coupled to a processor 310 to provide relative movement and/or orientation information which is independent of motion data derived from signals received by, for example, the transceivers 304 and/or 306, and the SPS receiver 308. By way of example but not limitation, motion sensor 312 may utilize an accelerometer (e.g., a MEMS device), a gyroscope, a geomagnetic sensor (e.g., a compass), an altimeter (e.g., a barometric pressure altimeter), and/or any other type of sensor. Moreover, motion sensor 312 may include a plurality of different types of devices and combine their outputs in order to provide motion information. Measurement data from the motion/orientation sensor(s) 312 representative of the motion/orientation of the user may also be used to instruct/direct the user in accordance with that motion/orientation information. For example, a motion/orientation sensor to determine the direction at which the user may be looking (e.g., based on the tilt of the user's head, and the head's angular position relative to some reference point, as may be determined from motion/orientation sensors fitted, for example, on headgear worn by the user) can be used to direct the user to turn his/her head in a direction required to complete a particular task. For instant, if the user is tasked with collecting items in a warehouse, the user may be directed/instructed, based on measurements from sensor/orientation sensors, to turn his/her head in a direction where a particular item to be collected is located.

The processor (also referred to as a controller) 310 may be connected to the transceivers 304 and/or 306, the SPS receiver 308 and the motion sensor 312. The processor may include one or more microprocessors, microcontrollers, and/or digital signal processors that provide processing functions, as well as other calculation and control functionality. The processor 310 may also include memory 314 for storing data and software instructions for executing programmed functionality within the mobile device. The memory 314 may be on-board the processor 310 (e.g., within the same IC package), and/or the memory may be external memory to the processor and functionally coupled over a data bus. Further details regarding an example embodiments of a processor or computation system, which may be similar to that of the processor 310, are provided below in relation to FIG. 6.

The example device 300 may further include a user interface 350 which provides any suitable interface systems, such as a microphone/speaker 352, keypad 354, and display 356 that allows user interaction with the mobile device 300. As noted, such a user interface, be it an audiovisual interface (e.g., a display and speakers) of a smartphone such as the smartphone 120b of FIG. 1, a tablet-based device such as the tablet-based device 120a, or an audio interface such as the speakers of an earphone-based device such as the earphones 120c of FIG. 1, are configured to present instruction data to regulate the user's activity, generated by a remote system such as the system 130 or 200 of FIGS. 1 and 2, respectively, and/or generated by the device 300 itself, e.g., using the controller 310. The microphone/speaker 352 provides for voice communication functionality, the keypad 354 includes suitable buttons for user input, the display 356 includes any suitable display, such as, for example, a backlit LCD display, and may further include a touch screen display for additional user input modes. The microphone/speaker 352 may also include or be coupled to a speech synthesizer (e.g., a text-to-speech module) that can convert instruction data (which may have encoded as text instructions, or according to some predefined coding convention) to audio speech so that the user, in situations where an audio interface is used, can receive audio instructions generated based on coded instruction data. Such a speech synthesizer may be a separate module, or may be integrally coupled to the microphone/speaker 352 or to the controller 310 of the device of FIG. 3.

Figure 4:
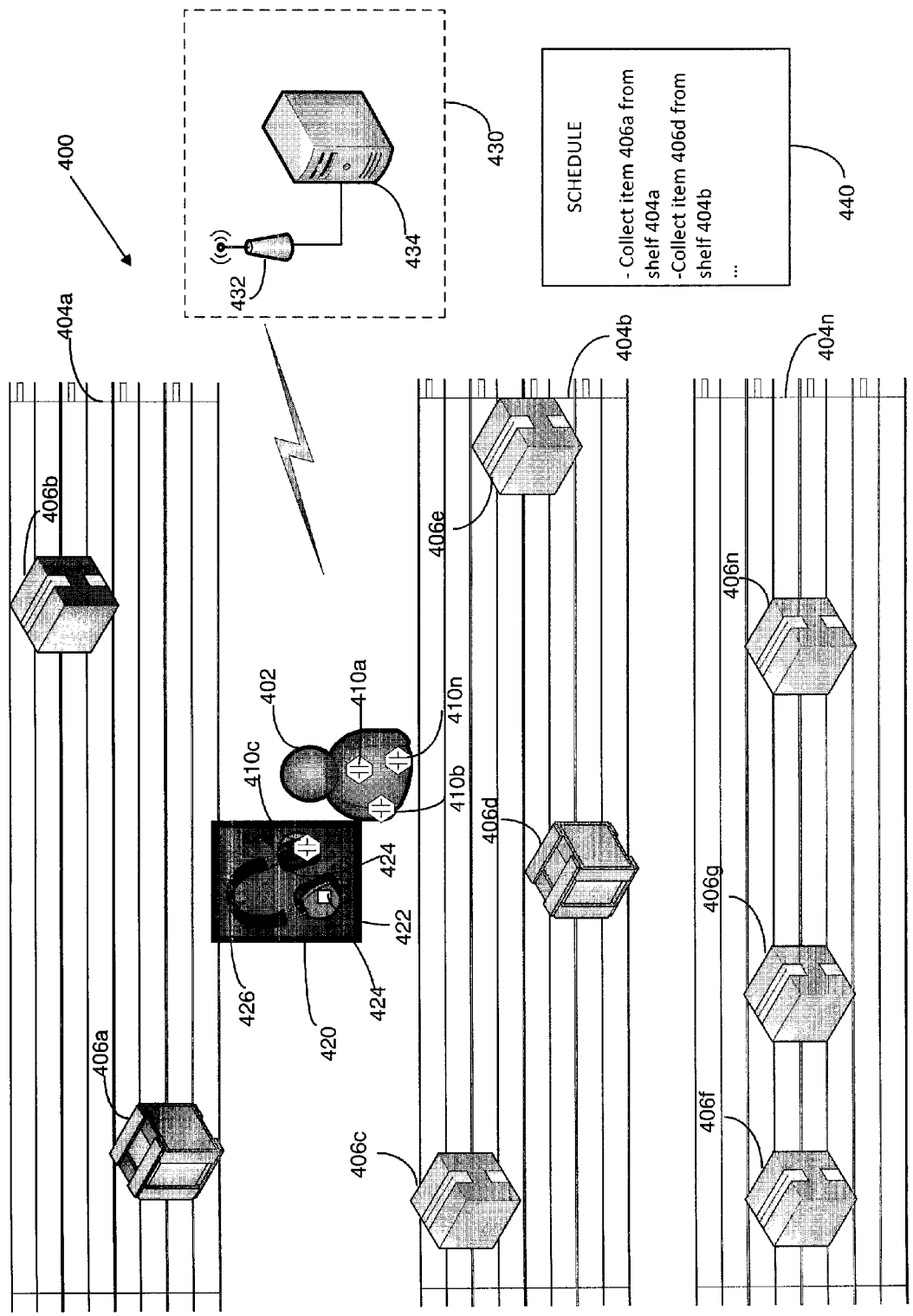
FIG. 4 is a diagram of an example warehouse environment in which an example system to regulate activities of a user working in the warehouse environment is deployed.

To illustrate operations to regulate activities of a user based on biometric data of the user from biometric sensors, reference is made to FIG. 4 showing an example environment 400 in which an example system to regulate activities of a user working in a warehouse is deployed. The system regulating the activities of the user may be deployed in many other types of environments, and may be used to regulate many other types of activities. The environment 400 includes a warehouse in which shelves 404a-n are arranged, and on which various items 406a-n (represented as boxes and crates) are placed. A user 402 is tasked with collecting/picking and distributing various items. The user is equipped with an audio and/or visual interface 420, which in the example of FIG. 4 includes earphones-type audio interface through which various instructions pertaining to the user's assigned tasks are presented to the user. Other interfaces may be used in addition to, or instead of, the interface 420. Instructions presented to a user may include not only which items to pick from, or drop off at, the various shelves of the warehouse, but additional instructions configured to regulate the picking/dropping-off activities undertaken by the user based on biometric data collected from the user. The interface 420 may be configured and have functionality that may be similar to, at least in part, the configuration and functionality of any of the interfaces 120a-c depicted in FIG. 1 and/or the device 300 depicted in FIG. 3. Thus, in some embodiments, the interface 420 may include, for example, a communication module (e.g., a wireless or cellular transceiver) to communicate with a remote system (such as a remote system 430, which may be similar to the remote system 130 of FIG. 1, and/or the system 200 of FIG. 2), a processing unit 422 (controller) to process data collected from sensors or to perform at least some of the activity-regulating operations, motion/orientation sensors, devices to facilitate position-determination (e.g., SPS receiver, such as a GPS receiver), etc.

Coupled to the user 402 are one or more biometric sensors 410a-n, which may include, for example, a heart monitor, a blood-pressure monitor, blood-oxygen monitor, a thermistor, etc. As shown in FIG. 1, at least one of the biometric sensors, e.g., biometric sensor 410c, may be positioned on or inside a housing of the interface 420. Thus, in the example of FIG. 4 in which an earphone-type interface is used, the at least one of the biometric sensors may be placed near the speaker portion of the earphone so that when the earphone are placed over the user's ears, such a biometric sensor may make contact with the user's ear, or with some other area of the user's head near the ear, to thus easily engage the biometric sensor secured to the earphone housing to the user's ear or other part of the head. Such a sensor will continue being in contact with the user's ear, or other part of the user's head, as long as the earphones are worn by the user, and will become disengaged from the user when the earphones are removed. In some embodiments, one or more biometric sensors may be substantially enclosed inside a housing 424 of the earphones. In such embodiments, portions of the external surface area of the housing of the earphones that come in contact with the user may include sensing surfaces (e.g., electrodes) of the biometric sensor(s) substantially enclosed inside the housing of the earphones. As noted, one or more of the biometric sensors may be secured to other parts of the user 402. For example, as shown in FIG. 4, a sensor 410a may be a monitor (e.g., a heart monitor, a thermometer, etc.) that includes an electrode with an adhesive surface to adhere to the user's body. Another sensor may be worn on a belt secured to the user, and have a sensing surface that comes in contact with the user's body (e.g., at the user's hip).

In some embodiments, the user 402 may be equipped with a microphone (not shown) to enable verbal communication with another person (e.g., at the remote system 430). In such embodiments, a speech processor (implemented using, for example, a general controller/processor, or using a dedicated controller/processor) configured to analyze the speech of the user 402 to determine medical or biometric data therefrom may be used (such an arrangement may be referred to a speech sensor). For example, voice/speech processing applied to speech produced by the user 402 may be used to determine/detect abnormalities in the user's speech, such as slurring, unsteadiness (which may be indicative of physical over-exertion on the part of the user), other types of auditory degradation, as well as other speech-related attributes. The user's speech may be compared (or otherwise processed) relative to a speech baseline previously collected for the user. Biometric data determined from speech produced by the user and communicated via a microphone may thus be used as another biometric measurement of a biometric attribute (namely, a person voice/speech) based on which activities performed by the user (and/or other users) may be regulated. In some embodiments, another sensor that may be used is a breath sensor configured to measure features associated with the user's breath. Such a breath sensor may be fitted, for example, on a microphone that is placed proximate to the user's mouth to thus enable breath samples exhaled by the user to be sensed/measured. A breath sensor may be configured to measure the breathing rate and/or pattern of the user, based on which a determination regarding the user's medical condition may be made. For example, detection of a labored breathing pattern by the user may be indicative of physical distress, and as a result of which the user's activities may be regulated (e.g., to decrease them). A breath sensor may also be configured, in some embodiments, to measure the chemical content of breath samples, based on which measurements a determination may be made regarding the user's physical condition. For example, the user's blood-alcohol level may be determined based on breath samples detected by a breath sensor configured to interact with certain chemical(s) that may be found in a user's breath to thus enable determining a user's intoxication level.

Yet another biometric sensor that may be used to measure a user's biometric attributes is an optical sensor to measure a user's eye functionality/condition. For example, in implementations in which the interface used by the user includes a visual display (e.g., an interface such the interfaces 120a or 120b depicted in FIG. 1), the interface may also include an optical sensor (e.g., a camera or some other optical sensitive device) that can measure the optical performance of the user's eyes. For example, such a sensor (possibly in conjunction with a controller or some other processor) may be configured to measure the level of light reflection from the user's eyes, or to measure other attributes and behaviors associated with the user's eyes (retina, ocular nerves, etc.) Measured attributes related to the behavior/attributes of the user's eyes may also provide data on the basis of which the user's activities may be regulated. For example, measurements of the user's eyes revealing the presence of blood-shot eyes may indicate a physical/medical problem associated with the user, and on the basis of that determination changes to the activities being performed by the user may be made. Other sensors to measure users' various other biometric attributes may also be used.

With continued reference to FIG. 4, the one or more biometric sensors may be in communication with one or more communication modules (e.g., a transceiver to communicate signals according to various types of communications protocols), where some of the sensors may have their own dedicated communication module, while other of the sensors may share a global communication module. Such sensors may communicate measurement data to, for example, a controller (processing unit) positioned on one of the accessories/items carried by the user. For example, the sensors may communicate data to a processing unit/controller 422 (which may be positioned on or inside the structure constituting the interface 420, e.g., on or inside the housing 424 of the earphones, on or inside a housing 426 of a headpiece of the interface 420, etc.) The processing unit/controller 422 may process the measurement data, and based on the measurement data generate instruction data presentable to the user (e.g., via the earphones) to regulate the user's item picking and distribution activities. Additionally and/or alternatively, the processing unit/controller 422 or may cause the data (or some processed portion of it) to be communicated to the remote system 430 via a transceiver (not shown in FIG. 4), which may also be positioned on or inside the housing constituting the interface 420. The remote system 430 may, based on such received data, perform at least some of the processing to generate instruction data that is to be communicated back to the interface 420 and presented to the user.

As noted, a user's biometric data is used, at least in part, to generate instruction data relating to the user's activities (item picking and distribution in the example of FIG. 4). In some variations, generating the instruction data may include revising some initial schedule (such as the schedule 440 illustrated in FIG. 4) prepared for the user to pick-up and distribute items. Such an initial schedule may specify what items need to be picked up or delivered to specific locations in the warehouse of the environment 400. For example, the schedule can specify that item 406*d* needs to be picked up from shelf 404*b*. The schedule may additionally specify that the tasks should be completed within a pre-set time period. The tasks that need to be completed within the initial pre-set period of time may thus define goals that the user 402 is expected to achieve. The schedule may specify the instructions presentable to the user, or may include information used to generate instructions presentable to the user to direct the user as to what tasks need to be performed in the course of completing the user's assigned schedule. For example, schedule data indicating that the item 406*d* needs to be picked up from the shelf 404*b* may be used to generate verbal instructions that are communicated to the user's interface (the interface 420 in the example of FIG. 4) to direct the user to the shelf 404*b* (and may provide the user with a more specific location at the shelf 404*b*).

The initial schedule may be dynamically revised in accordance with the user's biometric data representative of the user's measured biometric attributes to adjust the schedule to the user's specific physical condition. For example, in response to a determination, based on the biometric data, that the user is becoming overly exerted or fatigued, the schedule may be adjusted in a manner that would enable the user's normal conditions (e.g., heart rate, breathing rate, temperature, etc.) to be restored. An adjustment of the schedule to restore a user's normal physical condition may be achieved by reducing the assigned tasks in the schedule, or allotting more time for completing the same pre-set tasks. The instructions data generated from the revised schedule may thus cause the pace or rate at which the user was working to be slowed down. In some embodiments, in response to an adjustment of the schedule to reduce the user's goals, instruction data may be generated specifically directing the user to slow down. Conversely, in some embodiments, if biometric data indicates that the user is performing at a pace lower than the user's true physical abilities, the user's schedule may be revised to increase the user's goals (e.g., adding more tasks, and/or decreasing the time period allotted for completing the user's tasks), and, as a result, instruction data would be generated that causes the user to operate at an increased physical level.

In some embodiments, a determination of the user's level of exertion may be determined by comparing the biometric data to predetermined threshold values, and/or by determining that the biometric data has deviated by some predetermined deviation value from a baseline value (which may be associated with the particular user). In some embodiments, a determination that the value of one (1) biometric attribute has exceeded its corresponding threshold (or is below its corresponding threshold in situations where worsening physical conditions result in decreases in particular biometric attributes) may trigger an adjustment of the schedule. In some embodiments, revision of the schedule may be triggered only if a predetermined number of biometric attributes' have been exceeded. For example, if two (2) abnormal physical/biometric attributes are required to trigger an operation to revise/regulate the user's activities, then a single abnormal biometric reading (e.g., heightened heart rate that exceeds the predetermined heart rate for the user) may not be, by itself, sufficient to cause a change of a schedule of activities determined for that user. However, if in addition to the heightened heart rate a biometric measurement of the user's body temperature indicates an abnormal reading (as determined, for example, from a comparison of the data representative of the measured body temperature to a predetermined temperature threshold), under these circumstances revisions to the user's activities schedule may be triggered.

As noted, worsening physical conditions of the user, as indicated by the user's biometric data collected by the biometric sensors applied to the user's body (e.g., coming in contact with the user's ear in a sensor fitted into or on the audio interface 420) may result in a dynamic adjustment of a schedule previously determined for the user 402 so as to reduce the number of tasks the user needs to perform in a particular time period and/or extending the particular time period allotted for completing the tasks specified in the schedule. Adjustment of the schedule will result in instruction data (which may have been generated automatically upon revising the schedule, or may have been generated subsequently, either at the remote system 430 or the controller 422) consistent with the revised schedule. For example, removal of a task from the schedule may cause generation of instructions directing the user to perform the remaining tasks on the revised schedule, and further directing the user to complete those tasks at the resultant decreased rate/pace. Thus, instruction data instructing the user to slow down when the user tasks or goals have been reduced may, in some variations, be generated.

In some variations, in response to a determination of worsening physical/medical condition of the user, at least part of the user's equipment (e.g., the interface 420 and/or some other equipment or accessories carried by the user) may be disabled. For instant, if a determination is made that data representative of measured biometric attribute of the user exceeds a predetermined health indicator (in situations where worsening of a user's physical or medical condition results in an increase in the measured level of a particular attribute), the user's equipment, like the interface 420, may be disabled, and, as a result, the user will no longer receive instruction data that could be presented to the user to direct the user to perform activities. For example, if the user's measured heart rate exceeds some predetermined heart rate threshold (e.g., 180 beats per minute, or some other value), the remote system 430 and/or the controller 422 (depending on which system/device controls operation of the user's equipment) may generate control signals to cause a particular user equipment (e.g., the interface 420) to become disabled so as to prevent the user from continuing performing activities. Thus, the interface 420 may stop presenting instructions to the user. In situations where worsening physical/medical condition is reflected in a decrease in a particular biometric attribute (blood pressure drops below a particular predetermined threshold that may be based on a user's personal characteristics, such as age, weight, gender, etc.), a determination that data representative of such an attribute is below the predetermined threshold will cause at least some of the user's equipment to be disabled. In some embodiments, in response to a worsening physical/medical condition of the user, an alert to a person or entity (e.g., emergency services) may be sent so that appropriate treatment is provided to the user.

In some implementations, the instruction data generated, at the remote system 430 and/or locally (e.g., at the controller 422 of the interface 420) may include not only the tasks that need to be completed (e.g., collecting or dropping off particular items) but also geographical directions to lead the user to the location where the pending task is to be performed. Providing geographical direction may be performed based on position of the user, determined in accordance with, for example, signals received by an SPS receiver (such as the SPS receiver 308 depicted in FIG. 3) or by a wireless transceiver (such as the transceivers 304 and/or 306 of FIG. 3) that are carried by the user (and may be part of the interface 420). Signals received from access points, base stations, or satellites can be used to establish the receivers precise or approximate position (e.g., based on multilateration position determination procedures). Using the determined location of the receiver(s) (and thus of the user) relative to the transmitting systems, the user's position with respect to a local map where the user is located (such a map may have been previously stored on a device carried by the user, or may have been stored in a storage device of the remote system 430) can be determined. Based on the user's position with respect to the local map, instructions/direction to various points in the local frame of reference in which the user is operating can be generated. For example, if the user is determined to be located at a position on a map of the warehouse that is close to the shelf 404a, and the next task on the schedule requires the user to pick up item 406f at shelf 404n, an instruction that may be generated that, when presented on the interface 420, audibly directs the user to proceed to shelf 404n in a particular direction (e.g., north, south, left, right, etc.) for a determined distance of X meters, to proceed in the aisle next the shelf 404n for a distance of Y meters, and pick up the item 406f. Different instruction/direction formats may be used to guide the user to the desired location. Thus, in some embodiments, generating instruction data may include generating location instructions presentable to the user to direct the user to one or more geographical locations where item collection and distribution operations (for a plurality of items) are performed, and such generated instructions may be based, in part, on signals received from one or more of, for example, a wireless access point, a cellular base station, one or more satellites of a satellite positioning system, etc.

As noted, in some embodiments, the user may be equipped with motion and/or orientation/spatial sensors (e.g., fitted onto the interface or secured in some other way to the user or to accessories carried by the user), and the particular direction at which the user may be looking at may be determined. Accordingly, instruction data provided to the user for presentation on the interface carried by the user may also include directions on locating an item that the user cannot seem to track. For example, if item 406e is located at the top most shelf of shelf row 404n, and the motion/orientation sensors indicate that the user's head is not reclined or extended in any way, then an instruction telling the user to look upwards (possibly at some computed angle) may be generated as part of the instruction data provided to the user. Where motion/orientation sensors are employed, the controller 422 and/or the remote system 430 may need to be provided with information about the user, such as the user's height, in order to properly determine direction at which the user should look at. Thus, in some variations, generating location instructions may include generating location instructions based on measured motion and/or orientation of the user.

In some implementations, at least some of the instruction data may be generated at a remote system (such as the remote system 430). Thus, in such implementations, data representative of the measured biometric attributes is transmitted, via the access point 432, to the server 434 of the remote system 430, where at least some of the instruction data (coded, or in a format that can be directly presentable on the interface 420) is generated based on the received biometric data. The instruction data generated at the server 434 is transmitted to a transceiver located at a device carried by the user (e.g., a transceiver, such as the transceivers 304 and/or 306 of FIG. 3, which may be part of the interface 420), whereupon the instruction data is presented on the interface (optionally, some processing of the instruction data received from the remote system 430 may be performed, for example, by the controller 422 of the interface 420, or by some other processor/controller, before being presented on the interface).

In some implementations, at least some of the instruction data is generated locally at one of the devices carried by the user, e.g., at the controller 422 of the interface 420. Thus, in such implementations, the controller 422 receives biometric data from the various biometric sensors applied to the user (including from a biometric sensor that may be fitted in or on the housing of the audio interface 420). The controller 422 generates the at least some of the instruction data based on that received biometric data. When the instruction data is generated entirely at the controller 422, it may not be necessary to transmit the biometric data to the remote system 430.

Figure 5:
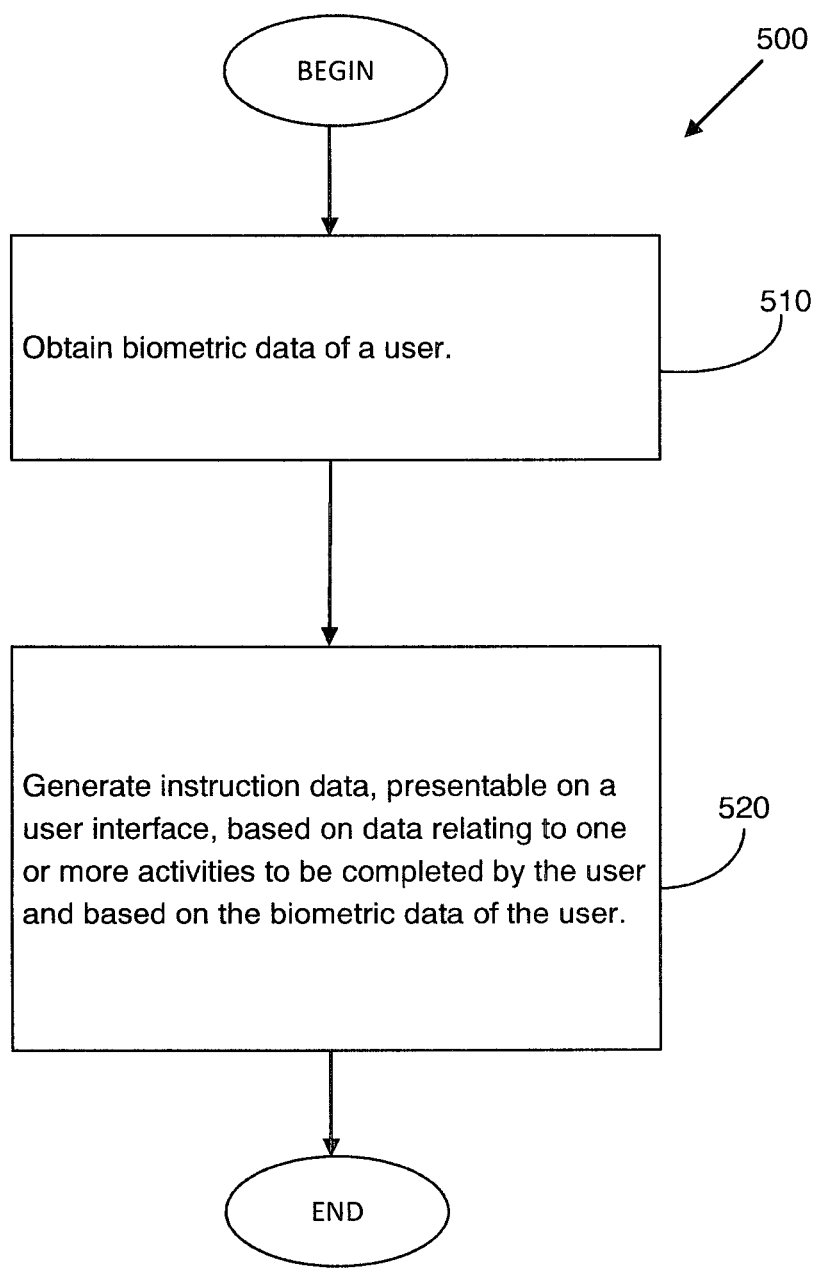
FIG. 5 is a flowchart of an example procedure to regulate a user's activities.

With reference now to FIG. 5, a flowchart of an example procedure 500 to perform activity regulation for users is shown. The procedure 500 includes obtaining 510 biometric data of a user. For example, in some embodiments, obtaining biometric data includes using one or more biometric sensors applied to a user's body to measure one or more biometric attributes of the users. Measurements made by the one or more sensors may be communicated to a processor(s) (which may be part of at least one of the one or more sensors), which may convert/derive a value provided through the measurement (e.g., a voltage value, or some other signal form) to data representative of the measured attribute. For example, body temperature may be measured using a thermistor-based sensor, whose resistance changes based on the measured temperature. A resistance of the thermistor (or a resultant voltage value) may be communicated to a processor and converted to data representative of the body's temperature corresponding to the measured value.

As further shown in FIG. 5, instruction/direction data, presentable on a user interface, (such as the interface 420 depicted and described in relation to FIG. 4, or any of the other interfaces described in the present disclosure) is generated 520 based on data relating to one or more activities to be completed by the user and based on the biometric data of the user. For example, in some embodiments, a processor-based device may receive a list of activities (which may be a global list) and the data representative of biometric attributes of the user. Based on the biometric attributes, a particular number of activities/tasks may be selected from the global list of activities and assigned to the user (e.g., if the data representative of the biometric attributes indicates a particular level of physical/medical condition, a number of tasks corresponding to that level may be assigned to the user). From the assigned tasks, corresponding instruction/direction data to be presented to the user to direct the user to complete the assigned tasks may be generated. Subsequent changes to the user's measured biometric attributes may result in revisions/adjustments to the activities to be performed by the user, and thus cause generation of instruction data consistent with those changed biometric attributes.

Performing the various operations described herein may be facilitated by a processor-based computing system. Particularly, each of the various systems/devices described herein may be implemented, at least in part, using one or more processing-based devices. Thus, with reference to FIG. 6, a schematic diagram of a generic computing system 600 is shown. The computing system 600 includes a processor-based device 610 such as a personal computer, a specialized computing device, and so forth, that typically includes a central processor unit 612. In addition to the CPU 612, the system includes main memory, cache memory and bus interface circuits (not shown). The processor-based device 610 may include a mass storage element 614, such as a hard drive or flash drive associated with the computer system. The computing system 600 may further include a keyboard, or keypad, or some other user input interface 616, and a monitor 620, e.g., a CRT (cathode ray tube) or LCD (liquid crystal display) monitor, that may be placed where a user can access them.

The processor-based device 610 is configured to facilitate, for example, the implementation of operations to generate instruction data, presentable on a user interface, based on data relating to one or more activities to be completed by the user and based on data representative of measured biometric attributes of a user. The storage device 614 may thus include a computer program product that when executed on the processor-based device 610 causes the processor-based device to perform operations to facilitate the implementation of the above-described procedures and operations. The processor-based device may further include peripheral devices to enable input/output functionality. Such peripheral devices may include, for example, a CD-ROM drive and/or flash drive (e.g., a removable flash drive), or a network connection (e.g., implemented using a USB port and/or a wireless transceiver), for downloading related content to the connected system. Such peripheral devices may also be used for downloading software containing computer instructions to enable general operation of the respective system/device. Alternatively and/or additionally, in some embodiments, special purpose logic circuitry, e.g., an FPGA (field programmable gate array), an ASIC (application-specific integrated circuit), a DSP processor, etc., may be used in the implementation of the system 600. Other modules that may be included with the processor-based device 610 are speakers, a sound card, a pointing device, e.g., a mouse or a trackball, by which the user can provide input to the computing system 600. The processor-based device 610 may include an operating system, e.g., Windows XP® Microsoft Corporation operating system. Alternatively, other operating systems could be used.

Computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a non-transitory machine-readable medium that receives machine instructions as a machine-readable signal.

Some or all of the subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an embodiment of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server generally arises by virtue of computer programs running on the respective computers and having a client-server relationship to each other.

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the embodiments and features disclosed herein. Other unclaimed embodiments and features are also contemplated. Accordingly, other embodiments are within the scope of the following claims.

What is claimed is:

1. A method comprising:

obtaining, by at least one processor-based device, biometric data for a user, including obtaining at least some of the biometric data via one or more biometric sensors housed in a user audio interface attachable to the user's ear; and dynamically adjusting by the at least one processor-based device, based on the biometric data, schedules of one or more physical activities that regulate a pace at which the one or more physical activities, selected from a global list of activities, are completed by a plurality of users, wherein dynamically adjusting the schedules of one or more physical activities includes performing one or more of:

removing from a pre-determined schedule of activities performable by the user at least one physical activity in response to a determination, based on the biometric data obtained for the user, of a physical condition problem experienced by the user, and assigning the at least one physical activity removed from the pre-determined schedule of the user to another user; or assigning to the pre-determined schedule at least one other physical activity, previously assigned to at least one other user, in response to another determination, based on the biometric data obtained for the user, that the physical condition of the user is normal and a further determination, based on additional biometric data obtained for the at least one other user, of at least one other physical condition problem experienced by the at least one other user.

2. The method of claim 1, further comprising:
determining the physical condition problem experienced by the user based on one or more of:
oxygen level measured for the user;
blood-shot eyes determined through eye sensor measurements;
blood-alcohol level determined based on chemical analysis of breath sample measured by a breath sensor; or
speech abnormalities detected based on a comparison of the user's speech to a previously obtained baseline speech sample.

3. The method of claim 1, wherein dynamically adjusting the schedules of one or more physical activities comprises:
generating based on, at least in part, the biometric data for the user, instruction data, comprising audible instruction data, presentable on the user audio interface attachable to the user's ear.

4. The method of claim 1, wherein obtaining the biometric data comprises:
measuring one or more of: heart rate, blood pressure, blood oxygen level, temperature, speech-related attributes, breath, and eye behavior.

5. The method of claim 1, wherein dynamically adjusting the schedules of one or more physical activities comprises:
revising an initial schedule for collecting and distributing a plurality of items at multiple geographical locations based on the biometric data for the user.

6. The method of claim 1, further comprising:
obtaining location data for the user;
wherein dynamically adjusting the schedules of one or more physical activities comprises:
dynamically adjusting the pre-determined schedule of the one or physical activities based, at least in part, on the biometric data obtained for the user and on the location data obtained for the user.

7. The method of claim 6, wherein dynamically adjusting the pre-determined schedule of activities based, at least in part, on the biometric data obtained for the user and on the location data obtained for the user comprises:
generating, based, at least in part, on the biometric data for the user and the location data for the user, instruction data presentable on a user interface to regulate the pace to perform the pre-determined schedule of activities to be completed by the user at multiple locations.

8. The method of claim 7, wherein generating the instruction data comprises:
generating location instructions presentable to the user to direct the user to the multiple locations where item collection and distribution operations for a plurality of items are performed.

9. The method of claim 6, wherein obtaining the location data for the user comprises one or more of:
determining a location of the user based, at least in part, on signals received from at least one of: a wireless access point, a cellular base station, and one or more satellites of a satellite positioning system; or
determining the location of the user based, at least in part, on measurements performed by one or more motion sensors.

10. The method of claim 1, further comprising:
disabling at least part of user equipment of the user based on a comparison of at least one of measured biometric attributes, represented by at least part of the obtained biometric data, to at least one corresponding predetermined health indicator threshold.

11. A system comprising:
one or more biometric sensors to measure biometric data for a user;
an audio interface attachable to at least one of the user's ears, the audio interface comprising at least one of the one or more biometric sensors coupled to a housing of the audio interface; and
one or more controllers to dynamically adjust, based on the biometric data, schedules of one or more physical activities that regulate a pace at which the one or more physical activities, selected from a global list of activities, are completed by a plurality of users, wherein the one or more controllers configured to dynamically adjust the schedules of one or more physical activities are configured to perform one or more of:
remove from a pre-determined schedule of activities performable by the user at least one physical activity in response to a determination, based on the biometric data obtained for the user, of a physical condition problem experienced by the user, and assign the at least one physical activity removed from the pre-determined schedule of the user to another user; or
assign to the pre-determined schedule at least one other physical activity, previously assigned to at least one other user, in response to another determination, based on the biometric data obtained for the user, that the physical condition of the user is normal, and a further determination, based on additional biometric data obtained for the at least one other user, of at least one other physical condition problem experienced by the at least one other user.

12. The system of claim 11, wherein the one or more controllers are further configured to:
determine the physical condition problem experienced by the user based on one or more of:
oxygen level measured for the user;
blood-shot eyes determined through eye sensor measurements;
blood-alcohol level determined based on chemical analysis of breath sample measured by a breath sensor; or
speech abnormalities detected based on a comparison of the user's speech to a previously obtained baseline speech sample.

13. The system of claim 11, further comprising:
a communication module configured to:
transmit to a server located remotely from the user the biometric data, the server comprising at least one of the one or more controllers; and
receive from the remotely located server instruction data presentable to the user to regulate the pace to perform the one or more physical activities, the instruction data generated remotely at the server.

14. The system of claim 11, wherein the one or more biometric sensors comprise one or more of: a heart rate monitor, a blood pressure monitor, a blood oxygen monitor, a thermometer, a speech sensor, a breath sensor, and an eye sensor.

15. The system of claim 11, further comprising:
a location determination device to obtain location data for the user;
wherein the one or more controllers configured to dynamically adjust the schedules of one or more physical activities are configured to:
dynamically adjust the pre-determined schedule of activities based, at least in part, on the biometric data measured for the user and on the location data obtained for the user.

16. The system of claim 15, wherein the one or more controllers configured to dynamically adjust the pre-determined schedule of activities based, at least in part, on the biometric data measured for the user and on the location data obtained for the user are configured to:
   generate, based, at least in part, on the biometric data for the user and the location data for the user, instruction data presentable on a user interface to regulate the pace to perform the pre-determined schedule of activities to be completed by the user at multiple locations.

17. A device comprising:
   an audio interface attachable to at least one ear of a user;
   one or more biometric sensors coupled to the audio interface, the one or more biometric sensors configured to measure biometric data for the user; and
   at least one controller to dynamically adjust, based on the biometric data, schedules of one or more physical activities that regulate a pace at which the one or more physical activities, selected from a global list of activities, are completed by a plurality of users, wherein the at least one controller configured to dynamically adjust the schedules of one or more physically activities is configured to perform one or more of:
   remove from a pre-determined schedule of activities performable by the user at least one physical activity in response to a determination, based on the biometric data obtained for the user, of a physical condition problem experienced by the user, and assign the at least one physical activity removed from the pre-determined schedule of the user to another user; or
   assign to the predetermined schedule at least one other physical activity, previously assigned to at least one other user, when it is determined, based on additional biometric data obtained for the at least one other user, of at least one other physical condition problem experienced by the at least one other user, and in response to another determination, based on the biometric data obtained for the user, that the physical condition of the user is normal.

* * * * *